United States Patent
Chae et al.

(10) Patent No.: US 11,891,354 B2
(45) Date of Patent: *Feb. 6, 2024

(54) TRICYCLODECANE DIMETHANOL COMPOSITION AND PREPARATION METHOD OF THE SAME

(71) Applicant: SK CHEMICALS CO., LTD., Gyeonggi-do (KR)

(72) Inventors: Hee Il Chae, Gyeonggi-do (KR); Ju-Sik Kang, Gyeonggi-do (KR); Jeong Ho Park, Gyeonggi-do (KR); Song Lee, Gyeonggi-do (KR); Yu Mi Chang, Gyeonggi-do (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/003,445

(22) PCT Filed: May 20, 2022

(86) PCT No.: PCT/KR2022/007238
§ 371 (c)(1),
(2) Date: Dec. 27, 2022

(87) PCT Pub. No.: WO2022/255696
PCT Pub. Date: Dec. 8, 2022

(65) Prior Publication Data
US 2023/0192577 A1 Jun. 22, 2023

(30) Foreign Application Priority Data
Jun. 4, 2021 (KR) .................. 10-2021-0072733

(51) Int. Cl.
*C07C 29/158* (2006.01)
*C07C 45/50* (2006.01)
*C07C 31/27* (2006.01)

(52) U.S. Cl.
CPC .......... *C07C 29/158* (2013.01); *C07C 31/278* (2013.01); *C07C 45/50* (2013.01)

(58) Field of Classification Search
CPC ...... C07C 31/278; C07C 29/158; C07C 45/50
See application file for complete search history.

(56) References Cited

U.S. PATENT DOCUMENTS

| 4,262,147 A * | 4/1981 | Garrou ............ C07C 29/16 568/817 |
| 6,365,782 B1 * | 4/2002 | Nakamura ........ C07C 29/141 568/822 |
| 6,794,482 B2 | 9/2004 | Gloeckner et al. |
| 6,939,997 B2 * | 9/2005 | Lappe ............ C07C 29/141 568/817 |
| 7,144,975 B2 | 12/2006 | Gloeckner et al. |
| 10,538,472 B1 | 1/2020 | Chou et al. |
| 10,767,004 B1 | 9/2020 | Chiu et al. |
| 2005/0107644 A1 | 5/2005 | Lappe et al. |
| 2005/0272960 A1 | 12/2005 | Dukat et al. |
| 2008/0039593 A1 | 2/2008 | Glockner et al. |
| 2021/0253507 A1 * | 8/2021 | Chae ............. C07C 45/50 |

FOREIGN PATENT DOCUMENTS

| JP | H11-080068 | * 3/1999 | ............ C07C 45/50 |
| JP | 2001-010999 | 1/2001 | |
| KR | 10-2005-0044847 | 5/2005 | |
| KR | 10-1200288 | 11/2012 | |
| KR | 10-2019-0142208 | 12/2019 | |
| KR | 10-2020-0136484 | 12/2020 | |
| KR | 10-2389695 | 4/2022 | |
| WO | WO 2020/164598 A1 * | 8/2020 | ........... C07C 29/141 |

OTHER PUBLICATIONS

JP H11-080068, Kuraray Co., Production of tricyclodecane dialdehyde, English translation, 6 pages (Year: 1999).*
International Search Report and Written Opinion for International (PCT) Patent Application No. PCT/KR2022/007238, dated Aug. 29, 2022, 6 pages.
Garlaschelli et al., "Hydroformylation and hydrocarbonylation of dicyclopentadiene with cobalt—rhodium catalytic systems promoted by triphenylphosphine: Synthesis of monoformyltricyclodecenes, diformyltricyclodecanes and di(tricyclodecenyl)ketones," Journal of Molecular Catalysis, vol. 68, 1991, pp. 7-21.
Lange et al., "Three times faster to gel point," Adhesion Adhesives & Sealants, vol. 13, 2016, pp. 14-19.

* cited by examiner

*Primary Examiner* — Yate' K Cutliff
(74) *Attorney, Agent, or Firm* — Sheridan Ross P.C.

(57) ABSTRACT

Provided are a tricyclodecane dimethanol composition which may be suitably used in preparing a polyester resin exhibiting excellent solvent resistance and chemical resistance when forming a coating film and having excellent solubility in organic solvents or water, and a preparation method thereof.

11 Claims, No Drawings

TRICYCLODECANE DIMETHANOL COMPOSITION AND PREPARATION METHOD OF THE SAME

CROSS-REFERENCE TO RELATED APPLICATION

This application is a national stage application under 35 U.S.C. 371 and claims the benefit of PCT Application No. PCT/KR2022/007238 having an international filing date of 20 May 2022, which designated the United States, and which PCT application claimed the benefit of Korean Patent Application No. 10-2021-0072733, filed on Jun. 4, 2021, the contents of each of which are incorporated herein by reference in their entireties.

TECHNICAL FIELD

The present invention relates to a tricyclodecane dimethanol composition, in which the content of $C_{11-12}$ diol compounds is controlled, and a preparation method thereof.

Background Art

Tricyclodecane dimethanol (3(4), 8(9)-dihydroxymethyl-tricyclo[$5.2.1.0^{2,6}$]decane, TCDDM) is a material used as a monomer in the preparation of polymers such as polyester, polyacrylate, etc.

Tricyclodecane dimethanol may be prepared by performing hydroformylation of dicyclopentadiene (DCPD) to prepare tricyclodecane dialdehyde (TCDDA), followed by hydrogenation thereof, as disclosed in Korean Patent No. 10-1200288.

TCDDM prepared by such a method is a mixture of various structural isomers and stereoisomers, and a polyester resin prepared using the same is characterized in that its crystallization is difficult. Therefore, it is suitable for use as a coating agent for coating the inner surface of a can, etc. When resins for use in coating have good solubility in organic solvents or water, it is preferable in that they may exhibit high processability. After a coating film is formed, the coating film should not be corroded or damaged even when exposed to solvents. Accordingly, it is necessary to develop a TCDDM composition capable of producing a polyester resin suitable for use as a coating agent for the inner surface of a can.

Prior Art Document

Patent Document 1: Korean Patent No. 10-1200288

DISCLOSURE

Technical Problem

There are provided a tricyclodecane dimethanol composition which may be suitably used in preparing a polyester exhibiting excellent solvent resistance and chemical resistance when forming a coating film and having excellent solubility in organic solvents or water by controlling the content of $C_{11-12}$ diol compounds in the composition, and a preparation method thereof.

Technical Solution

To achieve the above objects, there is provided a composition including tricyclodecane dimethanol; and
one or more of $C_{11-12}$ diol compounds represented by the following Formula 1-1 and Formula 1-2,
wherein the total content of the $C_{11-12}$ diol compounds is 4% by weight to 20% by weight:

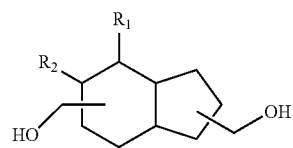

[Formula 1-1]

in Formula 1-1,
$R_1$ and $R_2$ are each independently hydrogen or methyl, provided that none of $R_1$ and $R_2$ is methyl,

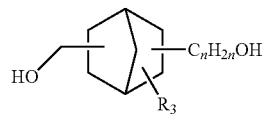

[Formula 1-2]

in Formula 1-2,
n is 3 or 4,
when n is 3, $R_3$ is hydrogen or methyl, and
when n is 4, $R_3$ is hydrogen.

There is also provided a method of preparing a composition, the composition including one or more of $C_{11-12}$ diol compounds represented by the following Formula 1-1 and Formula 1-2, wherein the content of the $C_{11-12}$ diol compounds is 4% by weight to 20% by weight, the method including the steps of:

performing a hydroformylation reaction by introducing a catalyst composition including a rhodium-containing catalyst compound and an organophosphorus compound into a reactor, and by adding dropwise dicyclopentadiene under a mixed gas of hydrogen and carbon monoxide; and performing a hydrogenation reaction of tricyclodecane dialdehyde obtained by the hydroformylation reaction in the presence of a hydrogenation catalyst, wherein the dicyclopentadiene includes 4% by weight to 20% by weight of co-dimers of $C_{4-5}$ diene and cyclopentadiene.

Effect of the Invention

A tricyclodecane dimethanol composition of the present invention satisfies the content of impurities in the form of $C_{11-12}$ diol within a predetermined range, thereby being suitably used in preparing a polyester having excellent solubility in organic solvents or water and having excellent solvent resistance and corrosion resistance when forming a coating film. Since the composition may be prepared from dicyclopentadiene having a relatively high content of impurity, it is economical without impairing physical properties of the polyester to be produced, such as a curing rate, strength after molding, etc., and therefore, the composition may be suitably used for coatings of metal substrates.

BEST MODE FOR CARRYING OUT THE INVENTION

Hereinafter, the present invention will be described in detail.

Tricyclodecane Dimethanol Composition

A composition of the present invention includes tricyclodecane dimethanol represented by Formula 2; and one or more of $C_{11-12}$ diol compounds represented by the following Formula 1-1 and Formula 1-2:

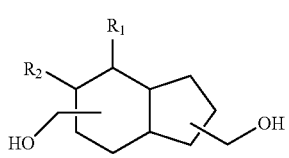

[Formula 1-1]

in Formula 1-1, $R_1$ and $R_2$ are each independently hydrogen or methyl, provided that none of $R_1$ and $R_2$ is methyl,

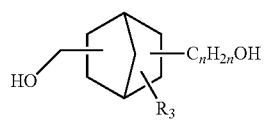

[Formula 1-2]

in Formula 1-2, n is 3 or 4, when n is 3, $R_3$ is hydrogen or methyl, and when n is 4, $R_3$ is hydrogen.

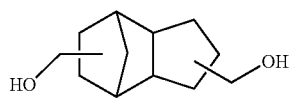

[Formula 2]

Tricyclodecane dimethanol (TCDDM) may be prepared by a preparation method including preparing tricyclodecane dialdehyde (DCDDA) by hydroformylation of dicyclopentadiene (DCPD), and then reducing DCDDA.

DCPD, which is a raw material used in the above preparation method, is usually prepared through dimerization of cyclopentadiene (Cp) obtained in a naphtha cracking process. Accordingly, in the cyclopentadiene raw material during the naphtha cracking process, $C_{4-5}$ diene compounds, for example, compounds such as butadiene, piperylene, isoprene, etc., may be present as impurities. The diene compound may form $C_{9-10}$ co-dimers by causing the Diels-Alder reaction with cyclopentadiene during the dimerization reaction of cyclopentadiene. Accordingly, the DCPD raw material includes a small amount of $C_{9-10}$ co-dimers as follows:

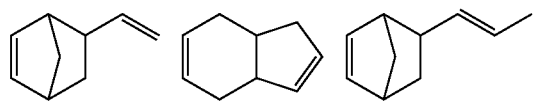

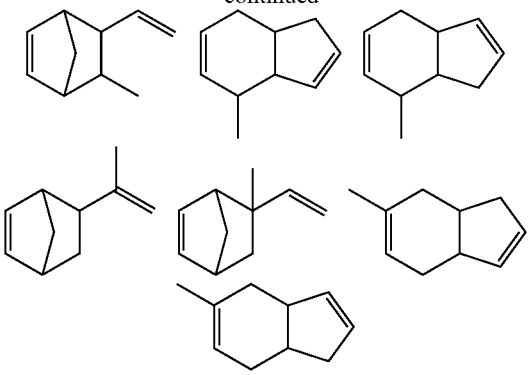

The co-dimers have two double bonds in the molecule, like DCPD, and thus a hydroformylation reaction may proceed, and through the subsequent hydrogenation reaction, they may be converted to the $C_{11-12}$ diol compound of Formula 1-1 or Formula 1-2.

Since such $C_{11-12}$ diol compounds are impurities, it has been previously recognized that as the content thereof is lower, the quality of TCDDM is better. However, according to the experimental results of the present inventors, it was found that when the content of the $C_{11-12}$ diol compound in the TCDDM composition is less than 4% by weight, the TCDDM composition with the lower content of $C_{11-12}$ diol compound may exhibit better performance, but when the TCDDM composition satisfying the content of $C_{11-12}$ diol compound in the range of 4% by weight to 20% by weight is included as a diol component to prepare a polyester resin, the solubility of the resin in organic solvents and water may be further improved without deteriorating the curing rate, high strength property of the resin. It was also found that when this resin is used to form a coating film, it may exhibit excellent solvent resistance and corrosion resistance.

Accordingly, the composition according to one embodiment of the present invention includes the $C_{11-12}$ diol compound in an amount of 4% by weight to 20% by weight. When the content of the $C_{11-12}$ diol compound in the composition is less than 4% by weight, it is difficult to obtain the effect of improving solubility of the polyester resin, as described above, and when the content is too high by exceeding 20% by weight, the curing rate of the polyester resin may be slowed due to a reduction in the purity of the composition, which may limit its use, and the strength may reduce, and the solvent resistance and corrosion resistance may significantly decrease when forming a coating film.

Meanwhile, the $C_{11-12}$ diol compound may be one or more selected from the group consisting of the following compounds:

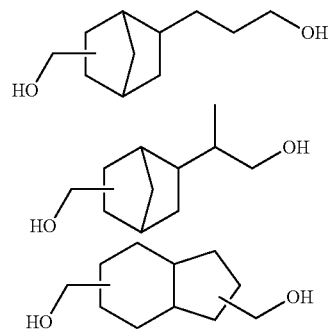

-continued

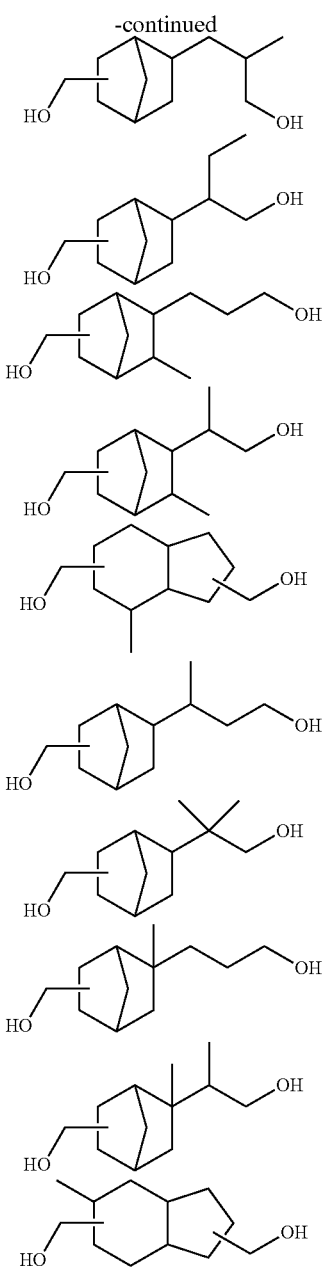

The contents of the TCDDM and the $C_{11-12}$ diol compound included in the composition may be identified by analysis of the composition through gas chromatography (GC). The gas chromatography analysis may be performed by, for example, the following method.

The composition is loaded onto a capillary column with a length of 30 m, an inner diameter of 250 μm and a film thickness of 0.25 μm. An oven is heated from an initial temperature of 100° C. to 200° C. at a rate of 10° C./min, then heated from 200° C. to 250° C. again at a rate of 3° C./min, and maintained for 30 minutes, and an inlet temperature is set to 300° C., and 1.0 μL of the sample is injected. Nitrogen is used as a carrier gas, a flame ionization detector (FID) is used as a detector, and a detector temperature is set to 260° C.

In the gas chromatography analysis, an elution peak of the $C_{11-12}$ diol compound is observed at a retention time of 21.1 min to 24.9 min, and an elution peak of the TCDDM is observed at a retention time of 25.4 min to 28.5 min. In this regard, the relative content of each compound may be derived by comparing the area of each peak with respect to the total area of the elution peak (excluding the solvent peak) of the TCDDM composition.

Meanwhile, the composition may include 79% or more, 80% or more, or 85% or more, and 96% or less of TCDDM, based on the total weight of the composition. The TCDDM may include a total of three types of structural isomers of 4,8-dihydroxymethyltricyclo[5.2.1.0$^{2,6}$]decane; 3,8-dihydroxymethyltricyclo[5.2.1.0$^{2,6}$]decane; and 3,9-dihydroxymethyltricyclo[5.2.1.0$^{2,6}$]decane, and a composition ratio thereof is not particularly limited.

Method of Preparing Tricyclodecane Dimethanol Composition

The tricyclodecane dimethanol composition satisfying the content of the $C_{11-12}$ diol compound in the range of 4% by weight to 20% by weight as described above may be prepared from dicyclopentadiene including co-dimers of $C_{4-5}$ diene and cyclopentadiene in an amount of 5% by weight to 10% by weight by a preparation method including the following steps:

i) performing a hydroformylation reaction by introducing a catalyst composition including a rhodium-containing catalyst compound and an organophosphorus compound into a reactor, and by adding dropwise dicyclopentadiene under a mixed gas of hydrogen and carbon monoxide; and ii) performing a hydrogenation reaction of tricyclodecane dialdehyde obtained by the hydroformylation reaction in the presence of a hydrogenation catalyst, Hereinafter, each step of the method of preparing the tricyclodecane dimethanol composition according to one embodiment of the present invention will be described in detail.

i) Step of Performing Hydroformylation Reaction of Dicyclopentadiene

The step i) is a step of preparing tricyclodecane dialdehyde (TCDDA) by performing hydroformylation of dicyclopentadiene (DCPD).

In the preparation method according to one embodiment of the present invention, dicyclopentadiene including co-dimers of $C_{4-5}$ diene and cyclopentadiene in an amount of 4% by weight to 20% by weight or 4.5% by weight to 19.5% by weight is used as a starting material in order to prepare a composition satisfying the content of $C_{11-12}$ diol compound as described above.

The $C_{4-5}$ diene may be butadiene, piperylene, or isoprene, and $C_{9-10}$ co-dimers produced by a reaction of the $C_{4-5}$ diene and cyclopentadiene are the same as described above.

The catalyst composition used in the hydroformylation reaction includes a rhodium-containing catalyst compound and an organophosphorus compound as a ligand.

The rhodium-containing catalyst compound applicable in the present invention is not particularly limited, as long as it exhibits the hydroformylation activity in the presence of hydrogen and carbon monoxide by forming a complex with the organophosphorus compound. For example, one or more selected from the group consisting of Rh(acac)(CO)$_2$, Rh$_2$O$_3$, Rh$_4$(CO)$_{12}$, Rh$_6$(CO)$_{16}$, Rh(NO3)$_3$, Rh/Al, and Rh/C may be used. Among them, Rh(acac)(CO)$_2$ may be preferably used.

In the known TCDDA preparation method, the rhodium compound is commonly used in an amount of 70 ppm to 300 ppm in order to increase the conversion rate. However, when it is used at such a high concentration, a separate process is further required to recover the expensive rhodium catalyst, and thus there has been a problem in that the efficiency and economic feasibility of the TCDDA preparation process are reduced. In contrast, in the present invention, since hydroformylation is performed by adding dropwise DCPD in small amounts without adding at once, it is possible to obtain excellent TCDDA conversion rate even with a significantly reduced amount of catalyst. Thus, a separate process of recovering the catalyst is not required, thereby greatly improving the efficiency of the process.

In the present invention, the rhodium-containing catalyst compound is preferably used in the range of 1 ppm to 50 ppm, or 10 ppm to 35 ppm, or 10 ppm to 20 ppm (based on the rhodium element) of the total weight of the reactant dicyclopentadiene. When the content of the rhodium-containing catalyst compound is less than 1 ppm relative to the weight of dicyclopentadiene, the amount of the catalyst is too small and the hydroformylation reaction does not properly occur, and therefore, the conversion rate may decrease. When the rhodium-containing catalyst compound is used in excess of 50 ppm, there may be a problem in that impurities due to side reactions are generated, and a separate process of recovering the catalyst is required. Thus, the above-described effect may not be achieved. For this reason, it is preferable to satisfy the above range.

The rhodium-containing catalyst compound may exhibit catalytic activity by forming a complex with the organophosphorus compound in the organic solvent. In this regard, the applicable organophosphorus compound may be phosphine, phosphite, etc., and preferably, phosphite having a formula of $P(OR^1)(OR^2)(OR^3)$ (wherein $R^1$, $R^2$, and $R^3$ are each independently a substituted or unsubstituted alkyl group or aryl group). Specifically, the organophosphorus compound may be one or more selected from the group consisting of triphenylphosphite, tris(2-t-butylphenyl)phosphite, tris(3-methyl-6-t-butylphenyl)phosphite, tris(3-methoxy-6-t-butylphenyl)phosphite, tris(2,4-di-t-butylphenyl)phosphite, and di(2-t-butylphenyl)phosphite, but is not limited thereto.

The amount of the organophosphorus compound may be adjusted according to the content of rhodium in the catalyst composition. In one embodiment, the organophosphorus compound is used in an amount of 5 moles to 200 moles per 1 mole of rhodium. When the content of the organophosphorus compound satisfies the above range, the content of the ligand per catalyst is sufficient, and thus the hydroformylation reaction may proceed smoothly. Preferably, the organophosphorus compound may be used in an amount of 10 moles or more, 15 moles or more, and 170 moles or less, 150 moles or less, 100 moles or less per 1 mole of rhodium.

The organic solvent applicable to the catalyst composition is not particularly limited, and commonly known inert organic solvents may be appropriately used. Specifically, the organic solvent may include aromatic hydrocarbon compounds, aliphatic hydrocarbon compounds, and alicyclic hydrocarbon compounds.

As the aromatic hydrocarbon compounds, methylbenzenes such as benzene, toluene, xylene, mesitylene, pseudocumene, etc., ethylbenzenes such as ethylbenzene, diethylbenzene, triethylbenzene, etc., propyl benzenes such as isopropylbenzene, 1,3-diisopropyl benzene, 1,4-diisopropyl benzene, etc., and other various alkyl benzenes may also be suitably used. As the aliphatic hydrocarbon compounds, pentane, hexane, heptane, octane, isooctane, dodecane, and decane may be exemplified, but they are not limited thereto, as long as they are a liquid at standard temperature and pressure. As the alicyclic hydrocarbon compounds, cyclohexane, cyclooctane, cyclododecane, decalin, methyl cyclohexane, etc. may be suitably used.

The concentration of the catalyst composition is not particularly limited, but it may be, for example, in the range of 0.01 mM to 5.0 mM, or 0.05 mM to 0.5 mM, based on the rhodium element. When the concentration of the catalyst composition is less than the above range, there may be a problem in that the catalyst reactivity deteriorates due to the excessively low concentration of the catalyst, and when the concentration exceeds the above range, there may be a problem in that the cost of the process increases due to excessive use of the catalyst. Accordingly, the concentration is properly controlled within the above range.

The hydroformylation reaction of DCPD is performed under a mixed gas atmosphere of hydrogen and carbon monoxide, wherein the pressure of the mixed gas is preferably maintained at 20 bar to 150 bar. When the reaction pressure is less than 20 bar, the hydroformylation reaction may not proceed smoothly, and when it exceeds 150 bar, a side reaction may occur to lower the TCDDA yield. More preferably, the pressure of the mixed gas may be 30 bar or more, or 50 bar or more, and 120 bar or less, or 100 bar or less.

In this regard, for smooth progress of the hydroformylation reaction, a volume ratio of hydrogen and carbon monoxide is preferably in the range of 1:10 to 10:1, more preferably, in the range of 1:2 to 2:1.

Under the pressure conditions as described above, the temperature of the hydroformylation reaction step is preferably 50° C. to 100° C., more preferably, 70° C. to 90° C., or 75° C. to 85° C. When the reaction temperature is lower than 50° C., smooth progress of the reaction may be difficult and the yield may decrease. When the reaction temperature is too high by exceeding 100° C., the retro Diels-Alder reaction of DCPD and Cp oligomerization by the Diels-Alder reaction of cyclopentadiene (Cp) generated by the retro Diels-Alder reaction and DCPD may occur.

Meanwhile, in the hydroformylation reaction step of the present invention, the raw material DCPD is added in a dropwise manner to the reactor including the catalyst composition, thereby achieving the excellent conversion rate even with a small amount of the catalyst and minimizing side reactions.

When DCPD is added in a dropwise manner, the concentration of DCPD relative to the concentration of the catalyst composition in the reactor is maintained low, and thus Cp oligomerization that may occur in the presence of a high concentration of DCPD may be suppressed. In addition, since the concentration of DCPD in the reactor may be controlled by controlling the dropwise addition rate, a high conversion rate may be achieved even with relatively small amounts of the catalyst compound and the ligand.

DCPD introduced into the reactor may be prepared in the form of a solution. In this regard, as the organic solvent, an organic solvent applicable to the catalyst composition may be used. The organic solvent used for the catalyst composition and the organic solvent used for the DCPD solution are not necessarily the same as each other, but it is preferable that the same solvent is used, because the reaction may smoothly proceed.

The concentration of the DCPD solution is not particularly limited, and for example, it may be in the range of 0.1 M or more, or 1.0 M to 7.6 M. When the concentration of the DCPD solution is less than the above range, the concentration of the rhodium-containing catalyst compound and the organophosphorus compound in the reactor decreases, as the dropwise addition proceeds, and thus there may be a problem in that the hydroformylation reaction does not proceed smoothly. Accordingly, the concentration is appropriately controlled within the above range.

The dropwise addition rate of DCPD may be controlled according to the concentration of the dicyclopentadiene solution and the capacity of the catalyst composition, and the number of moles of dicyclopentadiene added per minute with respect to 1 mmol of the catalyst (based on the rhodium element) of the catalyst composition is preferably allowed to be 10 mmol to 10,000 mmol, or 100 mmol to 1,000 mmol, or 100 mmol to 500 mmol.

When the dropwise addition rate is too fast by exceeding the above range, it is difficult to achieve the above-mentioned effect due to by-product generation, and when the dropwise addition rate is too slow, the overall reaction rate may become slow, and the process efficiency may be reduced. Accordingly, it is preferable to satisfy the above range.

The hydroformylation reaction time may be appropriately adjusted according to the reaction conditions and the contents of the reactants.

The reaction mixture including TCDDA which is obtained after the hydroformylation reaction undergoes a purification process such as vacuum distillation, etc., or only a thin film evaporation process to remove the solvent without a separate purification step, and then injected for the hydrogenation reaction. For example, the reaction mixture may be subjected to the thin film evaporation under a pressure of 0.1 torr to 10 torr, or 0.1 torr to 1 torr and a temperature of 90° C. to 150° C., or 100° C. to 120° C. to remove the solvent, followed by the hydrogenation reaction.

ii) Step of Performing Hydrogenation Reaction of Tricyclodecane Dialdehyde

Next, the tricyclodecane dialdehyde (TCDDA) mixture prepared through the hydroformylation reaction of the step i) is hydrogenated in the presence of a catalyst to prepare a tricyclodecane dimethanol (TCDDM) mixture.

The hydrogenation reaction may be performed in a solution. As the reaction solvent, a lower alcohol such as methanol, ethanol, isopropanol, etc., water, or a combination thereof may be used. For example, a mixed solvent of water and isopropanol may be used.

As the hydrogenation catalyst, a metal catalyst generally used for hydrogenation of a carbonyl group, for example, a metal catalyst, such as nickel, platinum, palladium, rhodium, ruthenium, copper, chromium, etc., may be used. The metal catalyst may be used in an elemental form, an oxide form, a form of being supported on an inorganic carrier, or a metal complex form. For example, as the hydrogenation catalyst, a ruthenium catalyst (Ru/C) supported on a carbon support may be used.

The amount of the catalyst used may be appropriately adjusted in consideration of the efficiency of the hydrogenation reaction. For example, the hydrogenation catalyst may be used in an amount of 50 ppm to 5000 ppm, or 100 ppm to 500 ppm with respect to the total weight of the reactant tricyclodecane dialdehyde mixture, based on the metal element. When the content of the catalyst is less than 50 ppm, the reaction rate may be too slow, and when the content exceeds 5000 ppm, the preparation cost increases due to excessive use of the catalyst without any particular advantage, and thus it is preferable to satisfy the above range.

The hydrogenation reaction may be performed at a temperature of 80° C. to 150° C. and a pressure of 50 bar to 100 bar, preferably, at a temperature of 90° C. to 130° C. and a pressure of 60 bar to 80 bar. When the reaction temperature is lower than 80° C., or the reaction pressure (the pressure of the hydrogen gas) is less than 50 bar, the reaction rate may not be sufficient. When the reaction temperature is higher than 150° C., or the reaction pressure is higher than 100 bar, deactivation of the catalyst may be accelerated, and process costs may increase.

After the hydrogenation reaction, a purification step may be performed, as needed. For example, the reaction mixture may be filtered to remove the solvent, and subjected to vacuum fractional distillation to obtain the tricyclodecane dimethanol composition. The fractional distillation may be performed, for example, under conditions of a pressure of 0.1 torr to 10 torr, or 0.1 torr to 1 torr and a temperature of 100° C. to 250° C., or 150° C. to 220° C.

The tricyclodecane dimethanol composition prepared by the above-described preparation method may include, together with tricyclodecane dimethanol, 4% by weight to 20% by weight of $C_{11-12}$ diol compound in the composition. A polyester produced by including the tricyclodecane dimethanol composition as a diol component may have excellent solubility in organic solvents and water, and a coating film produced using the polyester may exhibit excellent solvent resistance and corrosion resistance. Therefore, the tricyclodecane dimethanol composition of the present invention may be suitably used in preparing a polyester for coating metal substrates, such as the inner surface of a can, etc.

Hereinafter, the actions and effects of the present invention will be described in more detail with reference to the specific exemplary examples of the present invention. However, these exemplary examples are provided only for illustrating the present invention, and the scope of the present invention is not defined thereby.

EXAMPLE

Example 1

A TCDDM composition was prepared using DCPD (content of the co-dimer of $C_{4-5}$ diene and cyclopentadiene: 4.7%) with a purity of 95% by the following method.

(Step 1)

In a 1 L high-pressure reactor, 7.9 mg of $Rh(CO)_2(acac)$ (15 ppm, based on Rh, relative to dicyclopentadiene), and 2 g of tris(2,4-di-tert-butylphenyl)phosphite were dissolved in 100 g of toluene, and then the mixture was heated to 85° C. while maintaining a pressure of a mixed gas ($CO:H_2=1:1$) at 100 bar. A DCPD solution, in which 10 g of toluene and 210 g of dicyclopentadiene (DCPD) were mixed, was slowly added dropwise to the high-pressure reactor for 3 hours at a rate of 1.3 ml/min (i.e., the amount of DCPD added dropwise per minute with respect to 1 mmol of Rh was 320 mmol). During dropwise addition of the DCPD solution, the temperature and the pressure inside the high-pressure reactor were maintained at 85° C. and 100 bar, respectively. After completing the dropwise addition of the DCPD solution, the reaction was further allowed under the same temperature and pressure conditions for 1.5 hours.

(Step 2)

The reaction mixture in the step 1 without additional purification was further reacted for 3 hours while heating the mixture to 130° C. and maintaining the pressure of the $CO/H_2$ mixed gas at 100 bar. Then, a sample of the reaction mixture was taken and analyzed by gas chromatography.

(Step 3)

The reaction mixture of the step 2 was concentrated under reduced pressure to remove toluene. The toluene-removed mixture was subjected to thin film evaporation under conditions of 0.2 torr and 130° C. to obtain 281.1 g (yield: 92.0%) of TCDDA (TCD-dialdehyde).

(Step 4)

200 g of TCDDA of the step 3, 100 g of isopropyl alcohol (IPA), 25 g of water, and 3 g of 5% Ru/C (wetted with ca. 50% Water) were mixed and put into a 600 ml high-pressure reactor. The mixture was allowed to react for 4 hours while heating to 130° C. and maintaining a pressure of $H_2$ gas at 70 bar. Then, a sample of the reaction mixture was taken and analyzed by gas chromatography.

(Step 5)

The reaction mixture of the step 4 was filtered to remove Ru/C, and subjected to vacuum distillation under conditions of 100° C./10 torr to remove isopropyl alcohol and water. The TCDDM (TCD-dimethanol) mixture thus obtained was subjected to vacuum fractional distillation under conditions of 150° C. to 220° C. and 0.1 torr to obtain 181 g of a final TCDDM composition.

Example 2

A TCDDM composition was prepared in the same manner as in Example 1, except that DCPD (content of a co-dimer of $C_{4-5}$ diene and cyclopentadiene: 9.6%) with a purity of 90% was used.

Example 3

A TCDDM composition was prepared in the same manner as in Example 1, except that DCPD (content of a co-dimer of $C_{4-5}$ diene and cyclopentadiene: 14.5%) with a purity of 85% was used.

Example 4

A TCDDM composition was prepared in the same manner as in Example 1, except that DCPD (content of a co-dimer of $C_{4-5}$ diene and cyclopentadiene: 19.4%) with a purity of 80% was used.

Comparative Example 1

A TCDDM composition was prepared in the same manner as in Example 1, except that DCPD (content of a co-dimer of $C_{4-5}$ diene and cyclopentadiene: 2.3%) with a purity of 97% was used.

Comparative Example 2

A TCDDM composition was prepared in the same manner as in Example 1, except that DCPD (content of a co-dimer of $C_{4-5}$ diene and cyclopentadiene: 21.4%) with a purity of 78% was used.

Comparative Example 3

A TCDDM composition was prepared in the same manner as in Example 1, except that DCPD (content of a co-dimer of $C_{4-5}$ diene and cyclopentadiene: 24.6%) with a purity of 75% was used.

Comparative Example 4

A TCDDM composition was prepared in the same manner as in Example 1, except that DCPD (content of a co-dimer of $C_{4-5}$ diene and cyclopentadiene: 29.7%) with a purity of 70% was used.

[Gas Chromatography (GC) Analysis]

The contents of TCDDM and $C_{11-12}$ diol compound in each of the TCDDM compositions obtained in Examples and Comparative Examples were analyzed by gas chromatography.

Agilent 7890B (GC-FID) as an instrument and DB-WAX (length of 30 m×inner diameter of 250 μm×film thickness of 0.25 μm) model as a column were used, and an oven was heated from an initial temperature of 100° C. to 200° C. at a rate of 10° C./min. The temperature was again raised to 250° C. at a rate of 3° C./min, and maintained at 250° C. for 30 minutes, followed by analysis. An inlet temperature was 300° C., a detector temperature was 260° C., a flow rate was 1 mL/min, a split ratio was 30:1, a sample injection volume was 1 μl, and a carrier gas was nitrogen.

Detailed analysis conditions are as follows. An elution peak of the $C_{11-12}$ diol compound was observed at a retention time of 21.1 min to 24.9 min, and an elution peak of TCDDM was observed at a retention time of 25.4 min to 28.5 min. The content (% by weight) of each compound, based on 100% by weight of the TCDDM composition, was derived from the area of each peak with respect to the total area of the elution peak (excluding the solvent peak) of the TCDDM composition.

<Inlet>

Heater: 300° C., Pressure: 13.599 psi, Total Flow: 33 ml/min, Septum Purge Flow: 2 ml/min Split Ratio: 30:1

<COLUMN>

DB-WAX, 30 m×250 μm×0.25 μ, Agilent

Mode: constant flow, Nominal initial flow: 1.0 mL/min, Average velocity: 28.23 cm/sec

<DETECTOR (FID)>

Temperature: 260° C. (On), Hydrogen flow: 35.0 mL/min (On), Air flow: 350.0 mL/min (On), Makeup flow: 25.0 mL/min (On)

Makeup Gas Type: Nitrogen

TABLE 1

| | Purity of DCPD | TCDDM content (%) in composition | $C_{11-12}$ diol content (%) in composition |
|---|---|---|---|
| Example 1 | 95% | 95.2 | 4.3 |
| Example 2 | 90% | 89.7 | 10.0 |
| Example 3 | 85% | 85.1 | 14.4 |
| Example 4 | 80% | 79.9 | 19.2 |
| Comparative Example 1 | 97% | 97.2 | 2.1 |
| Comparative Example 2 | 78% | 78.3 | 21.1 |
| Comparative Example 3 | 75% | 75.1 | 24.5 |
| Comparative Example 4 | 70% | 69.6 | 29.1 |

[Preparation of Polyester Resin and Coating Composition including the Same and Evaluation]

(1) Preparation of Polyester resin

Polyester resins were prepared using each of the TCDDM compositions of Comparative Examples and Examples by the following method.

In a 2000 mL four-neck flask equipped with a thermometer, a condenser, a mantle, a stirrer, and a vacuum pump, 549.0 g of terephthalic acid and 6.3 g of trimellitic anhydride as an acid component, 117.9 g of 2-methyl-1,3-propanediol as a diol component, and 521.5 g of the TCDDM composition were placed, and tetrabutoxy titanium was added as an esterification catalyst.

When the mixture was slowly heated from room temperature (25° C.) to 240° C. under stirring and water or methanol as a by-product flowed out to a theoretical amount, tetrabutoxytitanium was added as a polycondensation catalyst, the temperature was raised to 260° C., and vacuum reaction was carried out for several hours. As a result, copolymerized polyester resins having an intrinsic viscosity of 0.40 dL/g to 0.65 dL/g and a number average molecular weight of 17,000 g/mol to 19,000 g/mol were obtained.

(2) Preparation of Coating Composition

The polyester resin prepared in (1) was diluted with a mixed solvent of Solvent naphtha-100/dibasic ester 50:50 (v/v) to obtain a resin solution with a solid content of 40% by weight, and additional components as shown in Table 2 below were blended therewith to prepare a coating composition.

TABLE 2

| Components in coating composition | Content (g) |
|---|---|
| 40% by weight of resin solution (solvent: Solvent naphtha-100/dibasic ester = 5:5, v/v) | 70 |
| 72% by weight of benzoguanamine resin solution (CYMEL 659, Allnex) | 9.7 |
| Solvent naphtha-100 | 10.2 |
| Dibasic ester | 10.1 |
| Dodecylbenzenesulfonic acid (CYCAT 600, Allnex) | 2.0 |

(3) Resin Solubility 10 g of the polyester resin prepared in (1) was added to 100 g of methyl ethyl ketone and dissolved therein under stirring at 60° C. for 1 hour. When a transparent homogeneous state was maintained, it was evaluated as good, and when a phase separation or cloudiness occurred, it was evaluated as insoluble.

(4) Evaluation of Coating Film

A tin-plated steel plate with a thickness of 0.3 mm was coated with the coating composition prepared in (2) at a thickness of 6 μm to 10 μm, and dried and cured at 210° C. for 10 minutes using an automatic ejecting oven to obtain a coating film. Solvent resistance and corrosion resistance of the coating film were evaluated by the following methods.

a) Solvent resistance: A soft cloth was soaked with methyl ethyl ketone, and wound around the fingers. The surface of the coating film was reciprocally rubbed with the cloth, and the number of reciprocations was counted until the coating film was damaged.

b) Corrosion resistance: After the coating film was subjected to an impact test (Dupont impact test), it was immersed in an aqueous solution containing 3% acetic acid and 3% NaCl, stored in an autoclave at 131° C. for 30 minutes, and then immersed in a copper sulfate solution for 60 minutes. Subsequently, the surface was divided into five areas having the same area, and the number of areas that were not corroded was counted. In other words, it was evaluated as 0/5 when all areas were corroded and 5/5 when no area was corroded.

TABLE 3

| TCDDM composition | Resin solubility | Solvent resistance | Corrosion resistance |
|---|---|---|---|
| Example 1 | Good | 53 | 5/5 |
| Example 2 | Good | 48 | 5/5 |
| Example 3 | Good | 47 | 5/5 |
| Example 4 | Good | 46 | 5/5 |
| Comparative Example 1 | Cloudiness occurred | 54 | 5/5 |
| Comparative Example 2 | Good | 23 | 3/5 |
| Comparative Example 3 | Good | 13 | 2/5 |
| Comparative Example 4 | Good | 8 | 2/5 |

Referring to Table 3, the polyester resins prepared using the TCDDM compositions of Examples 1 to 4 exhibited excellent solubility, and when the coating films were formed by using the same, they were found to have both excellent solvent resistance and corrosion resistance. In contrast, when the content of $C_{11-12}$ diol compound is less than 4%, as in Comparative Example 1, it was difficult to obtain the effect of improving solubility of the polyester resin, and when the content of $C_{11-12}$ diol compound is more than 20%, as in Comparative Examples 2 to 4, the solvent resistance and corrosion resistance of the coating films were found to be remarkably reduced.

What is claimed is:

1. A composition comprising tricyclodecane dimethanol; and
one or more of C11-12 diol compounds represented by the following Formula 1-1 and Formula 1-2,
wherein the total content of the C11-12 diol compounds is 10% by weight to 20% by weight:

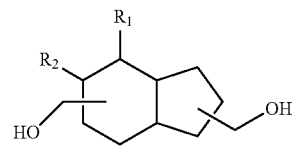

[Formula 1-1]

in Formula 1-1,
R1 and R2 are each independently hydrogen or methyl, provided that both R1 and R2 being methyl is excluded,

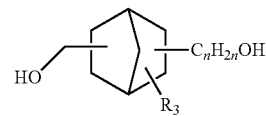

[Formula 1-2]

in Formula 1-2,
n is 3 or 4,
when n is 3, R3 is hydrogen or methyl, and
when n is 4, R3 is hydrogen.

2. The composition of claim 1, wherein the C11-12 diol compound is one or more selected from the group consisting of the following compounds:

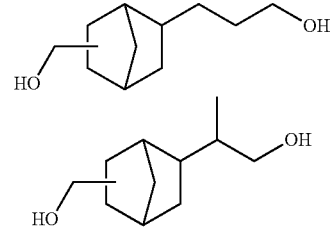

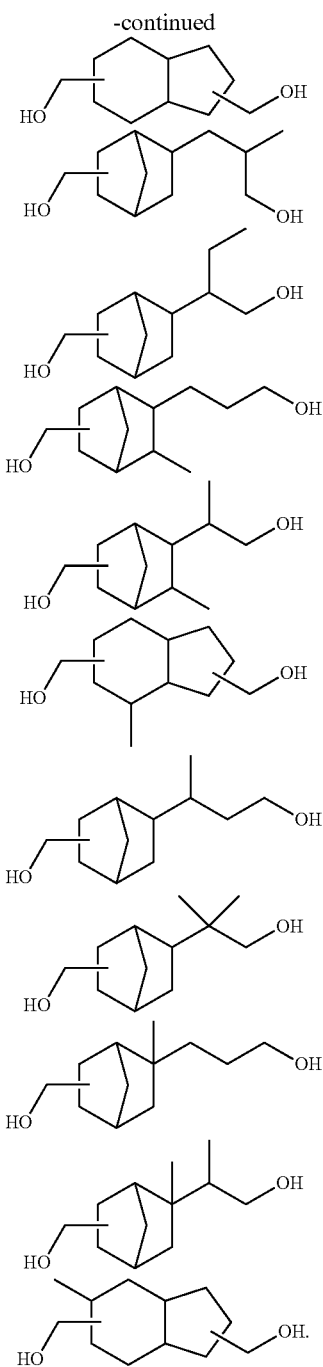

3. The composition of claim 1, wherein the tricyclodecane is included in an amount of 79% or more, based on the total weight of the composition.

4. A method of preparing a composition comprising tricyclodecane dimethanol; one or more of C11-12 diol compounds represented by the following Formula 1-1 and Formula 1-2, wherein the total content of the C11-12 diol compounds is 10% by weight to 20% by weight, the method comprising the steps of:
performing a hydroformylation reaction by introducing a catalyst composition including a rhodium-containing catalyst compound and an organophosphorus compound into a reactor, and by adding dropwise dicyclopentadiene under a mixed gas of hydrogen and carbon monoxide; and
performing a hydrogenation reaction of tricyclodecane dialdehyde obtained by the hydroformylation reaction in the presence of a hydrogenation catalyst,
wherein the dicyclopentadiene includes 4% by weight to 20% by weight of co-dimers of C4-5 diene and cyclopentadiene:

[Formula 1-1]

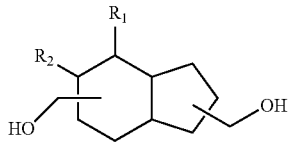

in Formula 1-1,
R1 and R2 are each independently hydrogen or methyl, provided that both R1 and R2 being methyl is excluded,

[Formula 1-2]

$$\text{HO} \quad \text{C}_n\text{H}_{2n}\text{OH} \quad R_3$$

in Formula 1-2,
n is 3 or 4,
when n is 3, R3 is hydrogen or methyl, and
when n is 4, R3 is hydrogen.

5. The method of claim 4, wherein the C4-5 diene is butadiene, piperylene, or isoprene.

6. The method of claim 4, wherein a pressure of the hydroformylation reaction step is 20 bar to 150 bar.

7. The method of claim 4, wherein a temperature of the hydroformylation reaction step is 50 °C. to 100 °C.

8. The method of claim 4, wherein the organophosphorus compound is included in an amount of 5 moles to 200 moles per 1 mole of rhodium.

9. The method of claim 4, wherein in the hydroformylation reaction step, the dropwise addition of dicyclopentadiene is performed such that the number of moles of dicyclopentadiene added per minute with respect to 1 mmol of the rhodium element in the catalyst composition is 10 mmol to 10,000 mmol.

10. The method of claim 4, wherein the hydrogenation catalyst is a Ru/C catalyst.

11. The method of claim 4, wherein the hydrogenation reaction is performed at a temperature of 80 °C. to 150 °C. and a pressure of 50 bar to 100 bar.

* * * * *